(12) United States Patent
Wang et al.

(10) Patent No.: US 6,465,067 B1
(45) Date of Patent: Oct. 15, 2002

(54) COMPOSITION AND PROCESS FOR MANUFACTURING PBT CATHETER BALLOONS

(75) Inventors: Lixiao Wang, Maple Grove; Jianhua Chen, Plymouth, both of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 14 days.

(21) Appl. No.: 09/706,266

(22) Filed: Nov. 3, 2000

Related U.S. Application Data

(60) Continuation of application No. 09/657,494, filed on Sep. 8, 2000, now abandoned, which is a division of application No. 09/034,431, filed on Mar. 4, 1998, now abandoned.

(51) Int. Cl.[7] .......................... B29D 22/02; A61M 29/02
(52) U.S. Cl. .......................... 428/35.7; 428/36.9; 428/9; 604/96.01; 606/192
(58) Field of Search .................. 428/35.2, 36.91, 428/910, 920, 921, 36.9, 35.7, 35.4; 604/96.01, 192, 194, 101, 103; 606/192, 194; 284/512, 515, 516, 532

(56) References Cited

U.S. PATENT DOCUMENTS

| 4,380,621 A | 4/1983 | Nield et al. ................. 528/287 |
| 4,560,722 A | 12/1985 | Tyrell ............................ 524/405 |
| 4,713,407 A | 12/1987 | Bailey et al. ................ 524/109 |
| RE32,983 E | 7/1989 | Levy ........................ 428/36.92 |

(List continued on next page.)

FOREIGN PATENT DOCUMENTS

| EP | 0274411 | 7/1988 |
| EP | 0592885 A2 | 4/1994 |
| EP | 0745395 A2 | 12/1996 |
| EP | 0531117 B1 | 1/1997 |
| JP | 10-33659 | 10/1998 |
| WO | 96/04951 A1 | 2/1996 |
| WO | 97/32624 | 9/1997 |

OTHER PUBLICATIONS

Argus Chemical, Derwent 1977–81206Y, Abstract of BE 854443A.*
U.S. patent application Ser. No. 09/657494, L. Wang, et al., filed Sep. 8, 2000.
U.S. patent application Ser. No. 09/034431, Lixiao Wang et al., filed Mar. 04, 1998.

(List continued on next page.)

*Primary Examiner*—Harold Pyon
*Assistant Examiner*—Sow-Fun Hon
(74) *Attorney, Agent, or Firm*—Vidas, Arrett, Steinkraus, P.A.

(57) ABSTRACT

A processing technique and a composition which allow compositions of PBT polymers or copolymers to be formed into blow molded articles, especially medical balloons such as dilatation or stent placement balloons, from extruded tubular parisons. The process includes a longitudinal stretch step run at a temperature below the Tg of the polymeric material and a radial expansion step run at a temperature above the Tg of the polymeric material. During the longitudinal stretch step, the tubing is subjected to high internal pressure. In the composition a small amount of boric acid is added to the polybutylene terephthalate in a melt blend to give a formulation which has reduced crystallinity after extrusion and which can more readily fashioned into high strength blow molded articles than PBT by itself. Articles, which may be formed using the invention include medical device balloon articles in which the polymer consists essentially of PBT optionally blended with boric acid.

25 Claims, 1 Drawing Sheet

U.S. PATENT DOCUMENTS

| | | | |
|---|---|---|---|
| 4,963,313 A | 10/1990 | Noddin et al. | 264/573 |
| 5,128,404 A | 7/1992 | Howe | 524/456 |
| 5,195,969 A | 3/1993 | Wang et al. | 604/96 |
| 5,213,754 A | 5/1993 | Kawaguchi et al. | 264/544 |
| 5,264,260 A | 11/1993 | Saab | 428/35.5 |
| 5,270,086 A | 12/1993 | Hamlin | 428/35.2 |
| 5,290,306 A | 3/1994 | Trotta et al. | 606/194 |
| 5,304,340 A | 4/1994 | Downey | 264/521 |
| 5,306,246 A | 4/1994 | Sahatjian et al. | 604/96 |
| 5,316,016 A | 5/1994 | Adams et al. | 128/774 |
| 5,328,468 A | 7/1994 | Kaneko et al. | 604/96 |
| 5,330,428 A | 7/1994 | Wang et al. | 604/96 |
| 5,348,538 A | 9/1994 | Wang et al. | 604/96 |
| 5,358,486 A | 10/1994 | Saab | 604/96 |
| 5,512,051 A | 4/1996 | Wang et al. | 604/96 |
| 5,554,120 A | 9/1996 | Chen et al. | 604/96 |
| 5,556,383 A | 9/1996 | Wang et al. | 604/96 |
| 5,587,125 A | 12/1996 | Roychowdhury | 264/515 |

OTHER PUBLICATIONS

M. Gilbert et al , "Effect of Chemical Structure on Crystallization Rates and Melting of Polymers: Part I, Aromatic Polyesters", "*Polymer*" 13, 327–332 (Jul. 1972).

C.F. Pratt et al, "Comparative Study of Crystallization Rates by d.s.c. and Depolarization Microscopy", "*Polymer*", 17, 12–16(Jan. 1976).

"Encylopedia of Polymer Science and Engineering", *John Wiley& Sons*, vol. 12, 226–229, (1988).

E. Chang et al., "The Effect of Additives on the Crystallization of Poly(Butylene Terephthalate)," *Polymer Engineering and Science*, 18,932–936, (1978).

* cited by examiner

COMPOSITION AND PROCESS FOR MANUFACTURING PBT CATHETER BALLOONS

This application is a continuation of application 09/657,494, filed Sep. 8, 2000, now abandoned, which is a division of application 09/034,431 filed Mar. 4, 1998, abandoned.

BACKGROUND OF THE INVENTION

Devices having a balloon mounted at the distal end of a catheter are useful in a variety of medical procedures. A balloon reservoir may be used to deliver a biologically compatible fluid, such a radiologically opaque fluid for contrast x-rays, to a site within the body. Radial expansion of a balloon may be used to expand or inflate a stent positioned within the body. A balloon may also be used to widen a vessel into which the catheter is inserted by dilating the blocked vessel. For example, in the technique of balloon angioplasty, a catheter is inserted for long distances into blood vessels of extremely reduced diameter and used to release or dilate stenoses therein by balloon inflation. These applications require extremely thin walled high strength relatively inelastic balloons of accurately predictable inflation properties.

Dilatation balloons made from PET (polyethylene terephthalate) are well known and widely used for angioplasty, stent placement, treatments in the gastrointestinal, urethral, or reproductive tracts, and for other medical purposes. Other polymer materials have also been reported to be useful in such applications and some of those polymer materials have also been used commercially, for instance, polyethylene, polyvinyl chloride, Surlyn® polyethylene ionomer copolymer, nylon 12 and Pebax® polyamide-polyether-polyester block copolymer. In a number of references pertaining to the formation of dilatation balloons, PBT (polybutylene terephthalate) is mentioned as a suitable balloon material, alone or as one layer of a laminate balloon. Such statements may be found in EP 0 745 395 A2 (Ethicon); U.S. Pat. No. 5,270,086 (Hamlin); and U.S. Pat. No. 5,304,340 (Downey). To date, however, no reference has actually reported the preparation of a PBT dilatation balloon, or even a PBT balloon layer.

Balloons made from poly(butylene terephthalate)-block-poly(tetramethylene oxide) are described in U.S. Pat. No. 5,556,383 (L. Wang, et al), incorporated herein by reference.

In U.S. Pat. No. 5,316,016 there is described a diagnostic imaging balloon for use on catheters to obtain an image of the configuration of an internal lesion or other body structure. The balloon has a memory effect when inflated with a pressure in a certain low pressure range. The polymer material used to prepare the balloon is a blend of PBT and a non-crystallizing ethylene/cyclohexanedimethylene terephthalate copolyester. This document states that it may be possible to prepare such balloons using PBT alone but to date no such balloons have been prepared. The imaging balloons prepared according to this patent are not suitable for dilatation or for other high pressure applications.

A major reason why PBT has not been used to make such balloons is the extremely high crystallization rate which the polymer displays. The high crystallization rate of polybutylene terephthalate makes it especially suitable as a molding resin where rapid crystallization reduces mold residence time. However for articles which are prepared from an extruded parison by a blow molding process, use of PBT polymer material has proven to be extremely difficult or impossible. This is because even very rapidly quenched extrusions are typically so high in crystallinity that the parison cannot be further processed in a practical manner. Opacification of the parison, another effect of PBT's high crystallinity, may also have been perceived as a problem for quality control in a manufacturing process. References describing the crystallization rate of PBT and/or its impact on thermoforming applications include: M. Gilbert, et al., "Effect of Chemical Structure on Crystallization Rates and Melting of Polymers: Part 1. Aromatic Polyesters," Polymer, 13, 327–332 (7/72); E. Chang, et al., "The Effect of Additives on the Crystallization of Poly(Butylene Terephthalate)," Polymer Engineering and Science, 18, 932–936 (9/78); U.S. Pat. No. 5,213,734, Kawaguchi, et al. (5/93); and U.S. Pat. No. 5,128,404, Howe (7/92).

In U.S. Pat. No. 5,213,754 there is described a polyester container prepared from a melt molded film of a butylene terephthalate copolyester. The copolyester is prepared from terephthalic acid, 1,4-butane diol and an alkylene oxide adduct of a bisphenol compound. The copolyester is used to provide a lower crystallization rate compared to PBT homopolymer material, The lower crystallization rate taken together with specific subsequent processing steps allows a thermoformable sheet to be obtained.

In U.S. Pat. No. 5,128,404 blow moldable PBT blend compositions are prepared by melt blending a mixture consisting essentially of PBT, an ethylene copolymer containing epoxide groups and an ionomer obtained by neutralizing a (meth)acrylic acid functional polymer with $Na^+$ or $K^+$.

In U.S. Pat. No. 4,380,681 crystallization rate of alkaline carboxylate terminated PET is reported to have been increased by use of boric acid as a polymer additive or of sodium borate as a polymerization additive.

It would be desirable to be able to make medical balloons such as dilatation or stent placement balloons out of PBT because the material offers the potential of achieving strength properties similar to PET but with better rewrap and lesion crossing characteristics. There therefore exists a need for improved processing techniques or for improved formulations which allow formation of high strength PBT balloons.

SUMMARY OF THE INVENTION

The present invention relates, in one aspect, to a processing technique which allows compositions of PBT polymers or copolymers to be formed into blow molded articles, especially medical balloons such as dilatation or stent placement balloons, from extruded tubular parisons. The process includes a longitudinal necking step run at a temperature at or below the Tg of the polymeric material and a radial expansion step run at a temperature above the Tg of the polymeric material. A characterizing feature of the inventive process is that, during the longitudinal necking step, the tubing is subjected to high internal pressure.

In another aspect the present invention relates to novel PBT-containing formulations which provide improved blow molding processability while producing a high strength formed article. According to this aspect of the invention, it has been discovered that a small amount of boric acid added to the polybutylene terephthalate in a melt blend gives a formulation which has reduced crystallinity after extrusion, as evidenced by improved extrusion clarity, and which can more readily fashioned into high strength blow molded articles than PBT by itself.

While the processing and formulation aspects of the invention can be practiced independently of each other, in preferred embodiments of the invention they are practiced together.

The invention is also directed to articles, especially medical device balloon articles, formed by blow molding of a polymer composition in which the polymer consists essentially of PBT. Articles formed using the process of the invention and/or the PBT/boric acid formulation described herein are also within the scope of the present invention.

DETAILED DESCRIPTION OF THE INVENTION

Polymers

Figure 1:
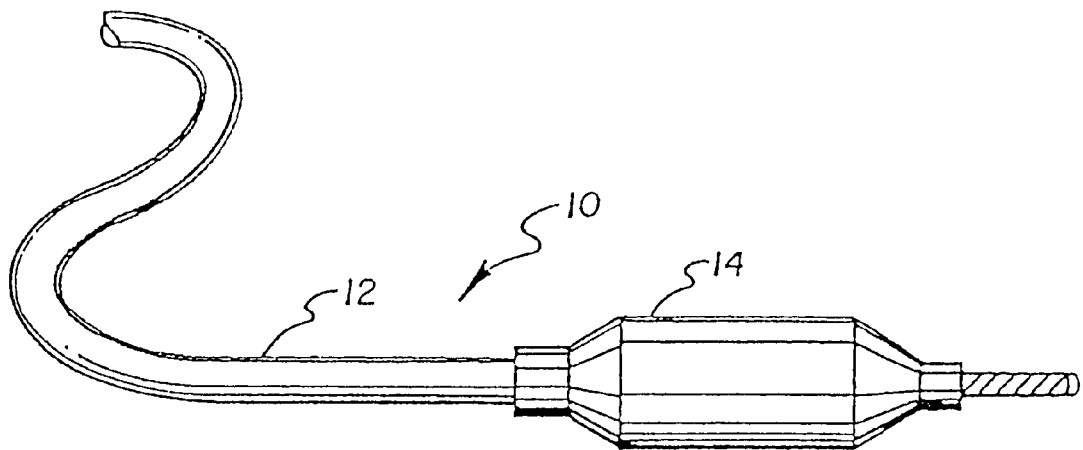
FIG. 1 is a perspective fragmentary view of a balloon catheter having a balloon thereon made in accordance with the invention.

The polymer materials which may be used in the invention have a high butylene terephthalate content. Such materials often display opacification when extruded and/or cannot be successfully blown after extrusion into a tubular parison. They include:

a) poly(butylene terephthalate) homopolymer, b) random polyester copolymers having above 80% butylene terephthalate repeat units, c) block copolymers comprising about 60% or more by weight of poly(butylene terephthalate), d) mixtures of at least two of a), b) and/or c); and e) mixtures of one or more of a), b) and/or c) with no more than 10% by weight of another polymer.

Examples of PBT homopolymers include Celanex 1600A, Celanex 1700A, both sold by Hoechst Celanese Corporation, and Ultradur B4500, and KR 4036, both PBT polymers sold by BASF. Polyester random copolymers with high butylene terephthalate content which also form whitened parisons on extrusion may also be used beneficially in the inventive process. Such copolymers will typically have at least 90% butylene terephthalate monomer units, more typically about 95% or more, and preferably at least 98%, butylene terephthalate monomer units. Block copolymers having PBT blocks constituting about 60% by weight or more, for instance PBT-polybutylene oxide block copolymers, may also be employed. Such block copolymers include segmented block copolymers sold under the Hytrel® and Arnitel® trademarks. Blends of PBT with up to about 10%, preferably no more than 5%, and more preferably no more than about 2%, of another polymer may also be usefully employed. Examples of polymers which can be included in such blends include other polyesters, such as PET; polyurethanes, especially polyurethanes derived from polyester polyols; polycarbonates, poly(meth)acrylates and maleate polymers.

Process

For catheter balloons, extrusions may be prepared according to conventional procedures used for other polymer materials such as PET, nylon or Pebax®.

The tube is then stressed in the axial direction at a temperature where necking occurs when axial stretching force is applied. Stressing in this manner starts a elongation of the tube from a specific point along its length where the tubing material is yieldingly pulled out until a specific diameter is reached, at which time the necking stops and material starts pulling successively from the adjacent unnecked region. In this way the point where the necking takes place propagates along the length of the tubing until the a sufficient length of the tubing segment to form a balloon has been necked down. Necking occurs when the material is stretched at a temperature which is about the Tg of the material, or lower. For a block copolymer the Tg referred to here is the highest Tg. At temperatures higher than about the Tg temperature, the material stretches uniformly, rather than by necking, when axially stressed. Typical necking temperatures will be in the range of 15–35° C., with ambient room temperature of about 20–25° C. usually being acceptable. The elongation produced by this process is a function of tubing wall thickness. For medical catheter balloons suited for dilatation or stent placement applications with nominal diameters of about 1.5–5.0 mm, extruded wall thicknesses in the range of 0.003–0.015 inch (0.076–0.38 mm) and outer diameters in the range of 0.015–0.055 inch (0.38–1.4 mm) will typically be suitable.

In accordance with the process of the present invention, the tubing is pressurized during the necking step. The pressure should be high, but not so high as to cause the parison to expand radially or burst during the stretch step. A typical pressure range for PBT homopolymer is from about 50 psi (345 kPa) to about 800 psi (5516 kPa), depending on wall thickness. Greater wall thickness will require greater pressure. For dilatation balloon extrusions suitable pressures will typically be in the range of from about 300 psi (2068 kPa) to about 500 psi (3447 kPa). Somewhat lower internal pressures during axial stretch may give beneficial results for copolymers or PBT polymer blends.

Following the longitudinal stretch step, the tubing is blown into an article such as a medical catheter balloon. Free blowing may be used, but typically a mold will be employed. Suitable radial expansion temperatures will usually be in the range of about 85–140° C., although in some cases temperatures as high as about 200° C. may be feasible. For medical catheter balloons internal pressure of about 250 (1724 kPa) to about 500 psi (3447 kPa) will generally be used to blow the balloon.

The two step process may be carried out in rapid sequence, for instance by inserting extruded tubing into a heated bath, promptly pressurizing and stressing to neck down the tubing before the tubing temperature exceeds the Tg of the material, and then blowing the balloon as the necked tubing segment nears or reaches the bath temperature. In some such cases it may be possible to maintain a constant pressurization of the tubing during the necking step, during the interval between necking and blowing, and during the blowing step.

Although the PBT polymer materials used in the present invention provide a balloon with a high rate of crystallization even when rapidly quenched following the blowing step, if desired, further crystallization can be accomplished by a heat setting step run at a temperature higher than the blow temperature (typically 5°–25° C. higher) but at a pressure lower than the blowing pressure (typically 30 psi (207 kPa) to about 100 psi (689 kPa). Heat setting can reduce balloon compliance and can increase the burst pressure of the balloon. Heat setting procedures which may be adapted for use in the inventive process are described in EP 274 411 A2 (C. R. Bard) and EP 592 885 A2 (C. R. Bard), both of which are incorporated herein by reference.

If it is desired to increase compliance or to provide a stepped compliance profile, the blown balloon may be slunk by heating to a temperature somewhat below the blowing temperature (suitably to about 70° C.–80° C.) while pressurizing to at about 30 psi (207 kPa) to about 100 psi (689 kPa). Shrinking procedures which may be adapted for use in the inventive process are described in U.S. Pat. No. 5,348,538 (L. Wang, et al) and in WO 97/32624, both of which are incorporated herein by reference.

Composition

Compositions of high butylene terephthalate content polymers which provide improved blow moldability from an extruded parison are also provided by the present invention. The compositions may be obtained by melt blending the polymer material with 0.01% to 5.0%, preferably from about 0.05 to about 0.5%, and more preferably from about 0.1% to about 0.3%, by weight of boric acid. The blend may be made in the extrusion melter or in a premelt prepared prior to extrusion. Suitable polymer materials are as described above. PBT homopolymer is preferred.

As boric acid is well tolerated by the body, and PBT is available in food contact grades, the use of the compositions of the invention to make medical devices, or packaging articles for food, cosmetic or pharmaceutical applications is not seen to raise new biocompatibility questions.

Articles

Both the process and the compositions of the invention provide benefits in obtaining high strength articles from PBT-based polymeric materials. The composition can be used to obtain blow molded articles by directly blowing an extruded tubular parison without any prestretching of the tubing. Conversely, the pressurized prestretch step has been demonstrated to allow balloon formation even in the absence of the boric acid additive of the inventive composition. However, when the process of the invention is practiced with a boric acid-containing composition of the invention, high strength products can be obtained at lower blow pressures than are required to form an article from a boric acid-free composition. The process and/or composition described above may be utilized to produce any kind of blow molded article for which it may be desirable to use PBT homopolymer or other high butylene terephthalate content polymer. Medical catheter balloons of diameters from about 1.25–40 mm, especially those in the range of about 1.5 to about 8 mm, are preferred articles to which the invention may be applied.

The balloons of the invention may be either single layer balloons, or multilayer balloons in which at least one layer is a high butylene terephthalate content polymer material as described above. The preferred 1.5–8 mm diameter dilatation balloons of this invention are suitably formed to provide a double wall thickness, measured on the uninflated collapsed balloon, of about 0.0004"–0.0025".

Multilayer Balloons

Known techniques for producing multilayer balloons may be readily modified to utilize a composition of the invention or the pressurized stretch step to thereby enable the employment of the PBT layer material. Various techniques are known for producing such multilayer structures, including coextrusion as described in U.S. Pat. No. 5,195,969 (J. Wang, et al.); U.S. Pat. No. 5,290,306 (Trotta et al); and U.S. Pat. No. 5,270,086 (Hamlin), and tube-in-tube techniques as described in copending U.S. application Ser. No. 08/611,664, filed Mar. 6, 1996; U.S. Pat. No. 5,512,051 (J. Wang, et al); and in WO 96/04951 (Schneider Inc.), all incorporated herein by reference.

In such multilayer balloons different high butylene terephthalate content polymeric materials may be employed as different layers of the same balloon, one or all of which may employ the boric acid additive. For instance, a multilayer laminate balloon may be provided from a coextruded tube having an inner layer of a PBT homopolymer/boric acid composition and an outer layer of a compatible poly(ester-block-ether) material which gives improved puncture resistance and/or a softer, less scratchy feel to give reduced vessel trauma in use.

Referring to FIG. 1 there is shown a catheter 10 comprising an elongated tube 12 with a balloon 14, made of a layer of PBT treated with boric acid in accordance with the invention hereof, mounted at the distal end thereof.

Figure 2:
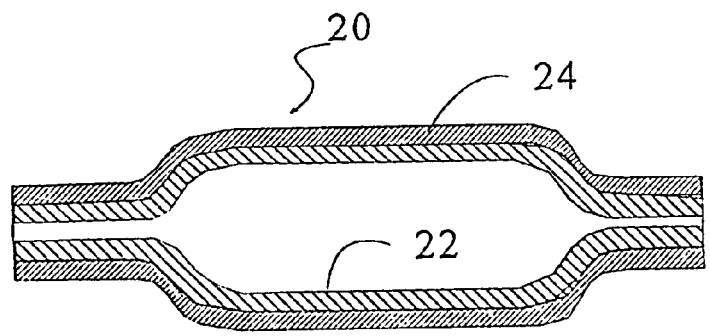
FIG. 2 is a side sectional view of a balloon in accordance with one embodiment of the invention.

Referring to FIG. 2 there is shown a catheter balloon 20 comprising an inner layer 22 of a PBT treated with boric acid as described herein, and an outer layer 24 of a relatively softer polymer such as a poly(ester-block-ether).

In addition to having one or more structural polymer layers, the balloon may be provided with a nonstructural coating layer, for instance a coating of a lubricious polymer or of a antithrombotic material, to improve surface properties of the balloon.

Those skilled in the art will recognize that other techniques known for preparing blow molded articles can be readily modified in accordance with the teachings and observations provided herein, and without undue experimentation, to produce blow molded articles of high PBT content polymers according to the present invention.

The invention is illustrated by the following non-limiting examples.

EXAMPLES

Attempts to form balloons were made using a number of different techniques and different polyester materials as shown in Table 1 below. The "yes" entries in Table 1 indicate that a balloon was formed. The "no" entries indicate that the technique did not produce a balloon. Examples 1–9 illustrate the procedures used.

Example 1

Comparative—PET Balloon (Stretched Above its Glass Transition Temperature)

PET tubing of ID 0.0171 and OD 0.0310 inch (made from Traytuf 7357, Shell Chemical) was stretched uniformly at 2.25 stretch ratio at 90° C. The stretched tube was inserted into a 3 mm balloon mold and the balloon was formed at 95° C. with a molding pressure of 300 psi and tension of 5 grams. The balloon burst at 230 psi with average balloon wall thickness of 0.00029 inch (double wall thickness was 0.00058). The distention from 6 atm to 12 atm was 5.8%.

Example 2

Comparative—PET Balloon (Without Stretch)

The same PET tubing (unstretched) used in Example 1 was inserted into a 3 mm balloon mold without stretching and a balloon was formed at 95° C. with the molding pressure of 180 psi (1241 kPa) and the tension of 20 grams. The balloon burst at 283 psi (1951 kPa) with average balloon wall thickness of 0.000445 inch (0.0113 mm) (double wall thickness was 0.00089 inch (0.0226 mm)). The distention from 6 atm to 12 atm (608–1216 kPa) was 3.4%.

Example 3

Comparative—PTT Balloon (Without Stretch)

PTT (poly(trimethylene terephthalate) Sam Yang Co., Korea) tubing of ID 0.0170 and OD 0.0370 inch was used to form a 3 mm balloon at 95° C. with the molding pressure of 170 psi and the tension of 5 grams. The balloon burst at 232 psi with average balloon wall thickness of 0.00068 inch (double wall thickness was 0.00136). The distention from 6 atm to 12 atm (608–1216 kPa) was 9.6%.

Example 4

PBT Balloon (Without Stretch, Thinner Wall Tubing)

PBT tubing of ID 0.0200 and OD 0.0300 inch (made from Celanex PET 1600A, Hoechst Celanese) was used to form a 3 mm balloon at 95° C. with the molding pressure of 250 psi. The balloon burst at 162 psi with average balloon wall thickness of 0.000315 inch (double wall thickness was 0.00063). The distention of 6/10 atm was 8.4%.

Example 5

PBT Balloon (Without Stretch, Boric Acid Modified, Thinner Wall Tubing)

Boric acid, 0.2% by weight, was added into PBT resin (Celanex PET 1600A, Hoechst Celanese) during tubing extrusion. The extruded tubing with ID 0.0200 and OD 0.0300 inch was used to form a 3 mm balloon at 95° C. with the molding pressure of 250 psi. The balloon burst at 169 psi with an average balloon wall thickness of 0.00030 inch (double wall thickness was 0.00060). The distention of 6/10 atm was 9.4%.

Example 6

PBT Balloon (Room Temperature Stretch Without Pressure, Boric Acid Modified, Thinner Wall Tubing)

The same tubing as in example 5 was used. The tubing of ID 0.0200 and OD 0.0300 inch was necked first at room temperature and then the necked portion was inserted into a 3 mm balloon mold. A balloon was formed at 95° C. with the molding pressure of 300 psi. The balloon burst at 184 psi with average balloon wall thickness of 0.000295 inch (double wall thickness was 0.00059). The distention of 6/10 atm was 9.7%.

Example 7

PBT Balloon (Stretch With Pressure, Regular Tubing Wall Thickness)

PBT tubing of ID 0.0170 and OD 0.0350 inch (made from Celanex PBT 1600A, Hoechst Celanese) was necked with 500 psi pressure inside. Then the necked portion was used to form a 3 mm balloon at 95° C. with the molding pressure of 320 psi and the tension of 5 grams. The balloon burst at 390 psi with average balloon wall thickness of 0.00067 inch (double wall thickness was 0.00134 inch). The distention from 6 atm to 12 atm (608–1216 kPa) was 3.9%.

Example 8

PBT Balloon (Stretch With Pressure, Boric Acid Modified, Regular Tubing Wall Thickness)

PBT tubing ID 0.0170 and OD 0.0350 inch (made from Celanex PBT 1600A, Hoechst Celanese, with 0.2% boric acid by weight introduced in extrusion process) was necked with pressure 400 psi inside tubing at room temperature. Then the necked portion was used to form a 3 mm balloon at 95° C. with the molding pressure of 390 psi and the tension of 5 grams. The balloon burst at 353 psi with average balloon wall thickness of 0.000675 inch (double wall thickness was 0.00135). The distention from 6 atm to 12 atm (608–1216 kPa) was 3.4%.

Example 9

PBT Balloon (Stretch With Pressure, Regular Tubing Wall Thickness)

PBT tubing of ID 0.0170 and OD 0.0350 inch (made from Ultradur B 4500, BASF) was necked with pressure 400 psi inside tubing at room temperature. Then the necked portion was used to form a 3 mm balloon at 95° C. with the molding pressure of 400 psi and the tension of 5 grams. The balloon burst at 364 psi with average balloon wall thickness of 0.000725 inch (double wall thickness was 0.00145). The distention from 6 atm to 12 atm (608–1216 kPa) was 3.6%.

TABLE 1

Effect of Different Polyester Balloon Forming Techniques and Compositions on Balloon Formation

| | | | | Materials (tubing size) | | | | | |
|---|---|---|---|---|---|---|---|---|---|
| | Stretch Condition | | Molding | PET | PTT | PBT 1600A | PBT 1600A Boric acid | PBT B-4500 | PBT 1600A | PBT 1600A Boric acid |
| Illustrative Example | Temp ° C. | Pressure psi | Pressure psi | (0.0171 × 0.0310) | (0.0170 × 0.0350) | (0.0171 × 0.0350) | (0.0171 × 0.0350) | (0.0171 × 0.0350) | (0.0200 × 0.0300) | (0.0200 × 0.0300) |
| 1 | 90 | — | <300 | yes | no | no | no | no | no | no |
| 2, 3 | none | — | <200 | yes | yes | no | no | no | | |
| 4, 5 | none | — | 200–300 | | | no | no | no | yes | yes |
| | none | — | 400–500 | | | no | no | no | | |
| 6 | 22 | — | 200–300 | no | no | no | no | no | no | yes |
| | 22 | — | 400–500 | no | no | no | no | no | no | |
| | 22 | 200–300 | 200–500 | no | no | no | no | no | | |
| | 22 | 400 | 200–300 | no | no | no | no | no | | |
| 8 | 22 | 400 | ~400 | no | no | no | yes | yes | | |
| | 22 | 500 | 200 | no | no | no | no | no | | |
| 7, 9 | 22 | 500 | 300–500 | no | no | yes | yes | yes | | |

Example 10

PBT, Celanex 1600A (Hoechst Celanese), with 0.2% by weight boric acid was extruded into a tube of inner diameter 0.0170 and outer diameter 0.0350 inch. The tube was stretched at room temperature and a speed of 12 sec/4 inch until fully necked. The tube was pressurized at 400 psi while it was stretched. The stretched tube was then inserted in a 3.00 mm balloon mold and a balloon formed at 95° C. with a blowing pressure of 300 psi and a tension of 30 grams.

Balloons prepared in this manner were subjected to standard burst tests. Burst strength and distension are given in Table 2.

Example 11

A stretched tube prepared in accordance with Example 10 was inserted in a 2.50 mm balloon mold and a balloon formed at 98° C. with a blowing pressure of 280 psi and a tension of 30 grams.

Balloons prepared in this manner were subjected to standard burst tests. Burst strength and distension are given in Table 2.

Example 12

A tube prepared in accordance with Example 10 was annealed at 110° C. for 1 hour before stretching and then stretched at a pressure of 420 psi. The stretched tube was inserted in a 2.75 mm balloon mold and a balloon formed at 98° C. with a blowing pressure of 350 psi and a tension of 30 grams.

Balloons prepared in this manner were subjected to standard burst tests. Burst strength and distension are given in Table 2.

Example 13

A tube of Arnitel EM740 block copolymer (poly(butylene terephthalate)-block-poly(tetramethylene oxide)) with 0.1% (by weight) boric acid was extruded into a tube of inner diameter 0.0230 and outer diameter 0.039 inch. The tube was stretched at room temperature with 200 psi pressure until fully necked. The stretched tube was inserted into a 3.00 mm balloon mold and the balloon formed at 95° C. with a blowing pressure of 300 psi and tension of 40 grams.

Balloons prepared in this manner were subjected to standard burst tests. Burst strength and distension are given in Table 2.

TABLE 2

Burst and Distention Test Results of Inventive Balloons

| Example | Double wall thickness (inch) | Burst pressure (psi) | Distention 6 atm–12 atm (608–1216 kPa) (%) | Distention 6 atm-burst (608 kPa-burst) (%) |
|---|---|---|---|---|
| 10 | 0.00125 | 323 | 3.7 | 9.8 |
| 11 | 0.00150 | 425 | 3.1 | 9.6 |
| 12 | 0.00120 | 338 | 3.7 | 12.1 |
| 13 | 0.00125 | 279 | 12.6 | 34.8 |

The process of the invention may also be usefully employed to form balloons of other polymers which have a very high crystallization rate, such as polypropylene, nylon 12, nylon 11, nylon 6, and injection molding grades of PET (the latter are typically formulated with a nucleating agent to accelerate crystallization).

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An article prepared by radial expansion of a hollow parison of a polymer composition at elevated temperature and pressure, wherein the polymer composition comprises a polymer material and 0.01–5.0% by weight of said polymer composition of boric acid, and wherein said polymer material is a member selected from the group consisting of
    a) poly(butylene terephthalate) homopolymer,
    b) random polyester copolymers-having above 80% butylene terephthalate repeat units,
    c) block copolymers comprising about 60% or more by weight of poly(butylene terephthalate),
    d) mixtures of at least two of a), b) and/or c); and
    e) mixtures of one or more of a), b) and/or c) with no more than 10% by weight of another polymer.

2. An article as in claim 1 wherein the polymer material has a butylene terephthalate content which opacifies extruded material in the absence of said boric acid.

3. An article as in claim 1 wherein said polymer material is poly(butylene terephthalate)homopolymer.

4. An article as in claim 1 wherein said polymer material is poly(butylene terephthalate)-block-poly(tetramethylene oxide).

5. An article as in claim 1 wherein the amount of boric acid is from about 0.05 to 0.5% by weight.

6. An article as in claim 1 wherein the amount of boric acid in said composition is from about 0.1 to 0.3% by weight.

7. An article as in claim 1 wherein the article is a balloon for a medical catheter.

8. An article as in claim 7 wherein the medical catheter device is a dilatation catheter.

9. An article produced by extruding a hollow parison of a composition, the composition consisting essentially of a polymer material mixed with 0.01 to 5% by weight of boric acid, wherein said polymer material is a member selected from the group consisting of
    a) poly(butylene terephthalate) homopolymer,
    b) random polyester copolymers having above 80% butylene terephthalate repeat units,
    c) block copolymers comprising about 60% or more by weight of poly(butylene terephthalate),
    d) mixtures of at least two of a), b) and/or c); and
    e) mixtures of one or more of a), b) and/or c) with no more than 10% by weight of another polymer;
    stressing the extruded hollow parison at a temperature at or below the Tg of the polymer while subjecting the parison to internal pressure under conditions which produce a propagating necking of at least a portion of the extruded parison; and then
    radially expanding the necked portion of the parison under pressure at a temperature above the Tg of the polymer material to form the article.

10. An article as in claim 7 wherein the article is a balloon for a medical catheter device.

11. An article as in claim 8 wherein the medical catheter device is a dilatation catheter.

12. An article as in claim 9 wherein the composition comprises 0.1–5% of said boric acid.

13. An article as in claim 9 wherein the amount of boric acid is from about 0.05 to 0.5% by weight.

14. An article as in claim 12 wherein the amount of boric acid is from about 0.1 to 0.3% by weight.

15. An article as in claim 9 wherein the polybutylene terephthalate content of said composition opacifies extruded material in the absence of said boric acid.

16. An article as in claim 9 wherein said polymer material is poly(butylene terephthalate) homopolymer.

17. An article as in claim 9 wherein said polymer material is poly(butylene terephthalate)-block-poly(tetramethylene oxide).

18. A balloon as in claim 11 wherein, after said radially expanding step, the balloon was subjected to a shrink step.

19. A balloon as in claim 11 wherein said parison comprises a layer of PBT homopolymer and a layer of a PBT block copolymer.

20. A balloon as in claim 19 wherein the PBT block copolymer is poly(butylene terephthalate)-block-poly(tetramethylene oxide).

21. A balloon as in claim 11 wherein, after said radially expanding step, the balloon was subjected to a heat setting step.

22. A balloon for a medical device formed from a polymer composition, wherein the polymer composition comprises a polymer material and 0.01–5.0% by weight of said polymer composition of boric acid, and wherein said polymer material is a member selected from the group consisting of
   a) poly(butylene terephthalate) homopolymer,
   b) random polyester copolymers having above 80% butylene terephthalate repeat units,
   c) block copolymers comprising about 60% or more by weight of poly(butylene terephthalate),
   d) mixtures of at least two of a), b) and/or c); and
   e) mixtures of one or more of a), b) and/or c) with no more than 10% by weight of another polymer.

23. A balloon as in claim 22 wherein the polymer material is poly(butylene terephthalate) homopolymer or a block copolymer comprising about 60% or more by weight of poly(butylene terephthalate).

24. A polymer composition comprising a single polymer material and 0.01–5.0% by weight of said composition of boric acid, said single polymer material being selected from the group consisting of
   a) poly(butylene terephthalate) homopolymer,
   b) random polyester copolymers having above 80% butylene terephthalate repeat units, and
   c) block copolymers comprising about 60% or more by weight of poly(butylene terephthalate);and wherein said polymer material has a butylene terephthalate content which opacifies extruded material in the absence of said boric acid.

25. An article prepared by radial expansion of a hollow parison of a polymer composition at elevated temperature and pressure, wherein the polymer composition comprises a polymer material and 0.01–5.0% by weight of said polymer composition of boric acid, and wherein said polymer material has a butylene terephthalate content which opacifies extruded material in the absence of said boric acid.

* * * * *